United States Patent
Carlgren

(10) Patent No.: US 6,666,878 B2
(45) Date of Patent: Dec. 23, 2003

(54) METHOD AND DEVICE STIMULATING THE ACTIVITY OF HAIR FOLLICLES

(75) Inventor: Stefan Carlgren, Stockholm (SE)

(73) Assignee: Inca Asset Management S.A., Geneva (CH)

( * ) Notice: Subject to any disclaimer, the term of this patent is extended or adjusted under 35 U.S.C. 154(b) by 0 days.

(21) Appl. No.: 09/874,358

(22) Filed: Jun. 6, 2001

(65) Prior Publication Data

US 2002/0188334 A1 Dec. 12, 2002

(51) Int. Cl.⁷ .................................................. A61N 5/01
(52) U.S. Cl. ............................... 607/91; 607/88; 607/89
(58) Field of Search ..................................... 607/88–89

(56) References Cited

U.S. PATENT DOCUMENTS

| | | | | |
|---|---|---|---|---|
| 5,228,431 A | * | 7/1993 | Giarretto | 601/11 |
| 5,616,140 A | * | 4/1997 | Prescott | 607/91 |
| 6,063,108 A | * | 5/2000 | Salansky et al. | 607/89 |
| 6,234,069 B1 | | 5/2001 | Palm | |
| 6,383,176 B1 | * | 5/2002 | Connors et al. | 606/13 |

FOREIGN PATENT DOCUMENTS

EP 0 130 950 B1 1/1985 ............ A61N/5/06

* cited by examiner

*Primary Examiner*—Roy D. Gibson
*Assistant Examiner*—Henry M. Johnson
(74) *Attorney, Agent, or Firm*—Sughrue Mion, PLLC

(57) ABSTRACT

A method of stimulating the hair follicles of a skin area by radiation of light.

The method including the following steps:
a. arranging a number of sources of light in a way so as to expose a portion of the area of skin to a field of light in the shape of a band, and
b. moving the band shaped field of light repeatedly over the area of the skin to be treated in order to create a pulsating stimulation of the hair follicles of the skin area.

The invention also relates to a device useable when carrying out the method.

12 Claims, 12 Drawing Sheets

METHOD AND DEVICE STIMULATING THE ACTIVITY OF HAIR FOLLICLES

FIELD OF THE INVENTION

The present invention relates to a method and device designed to stimulate and increase the natural activity of hair follicles. The invention relates to the field of skin therapy, restoration of hair production and wound healing originating from or assisted by the follicles. The invention consists of a method for the stimulation of follicles by applying light emanating from laser sources or from light emitting diodes to the skin. It also outlines the construction of alternative devices for the practical application of such light sources in a way to accomplish direct light rather than light distributed through fiber optic or other means as well as mechanical and electronic control methods to achieve an even distribution of the therapeutic light.

The skin in itself is the largest organ of the human body and the body of any mammal. As all functions and activities of the skin are not known to date intense research is continuing in the scientific community to uncover the mysteries of this important organ. The present invention constitutes an effort to put some of the data which is known today into practical use for the benefit of persons undergoing therapy according to the invention.

Being to a large degree an external organ, skin can be subjected to many forms of therapy including treatment with chemicals and ointments as well as vitamins, exposure to water, air and the sun, mechanical treatment and so forth. A number of things which our skin and the skin of any mammal is exposed to is not part of any treatment and constitutes more of a hazard to the skin than assisting its growth and recovery. In addition to such factors there are the internal workings and cellular activities of the skin as affected by various diseases and our general well being.

Apart from producing body hair, the hair follicles of humans and other mammals have an important role in the reproduction of skin cells in any part of the body and in the process of healing wounds to the skin. Indeed, future research may come to reveal that parts of the mysteries of aging are linked to the follicles.

Regardless of any future findings, it is known today that the follicles can be externally stimulated in order to increase or decrease their production of hair. Especially women are often concerned with unwanted body hair and various methods exist for the more or less permanent removal of such hair. In this context it is known that the action of simply ripping out a strand of hair may stimulate the follicle and increase the speed with which new hair is produced. Certain chemical treatments such as the treatment with the substance minoxidil may also constitute a stimulant. It is further known that laser treatment, regularly applied, causes the production of the follicles to decrease and eventually cease. The invention at hand is based on the fact that lasers as well as light emitting diodes can also be used as a positive stimulating agent if the treatment is carefully administered utilizing correct wave lengths, Periods of exposure and other such influencing factors.

The present invention directs itself to two major uses, both in relation to hair follicles: 1) The use of intermittent light from light emitting diodes lasers in the stimulation of and enhancement of the natural production of hair from the follicles by exposure to such lights (according to the invention, such light, correctly applied as to time, distance, intensity, wave length, pulsation of the light and preparation of the skin to be treated, stimulates and causes an increase in the hair production activity of the follicles), and 2) a similar use of intermittent light from the described sources which according to the invention assists cell reproduction emanating from the follicles thus assisting the skin in the process of healing.

BACKGROUND OF THE INVENTION

Hair follicles are small tubular cavities of the skin located in the subcutaneous layer beneath the dermis and extend from the surface of the skin down through the epidermal layers to a bulblike base where the hair is rooted. Each follicle supplies its hair with blood from a vein, an artery, and a papilla at the base. Associated with each follicle there are sebaceous glands, muscles and nerves. Follicles excrete oil and move dead skin cells to the surface of the skin apart from producing hair and assisting in the production of stem cells for the purpose of supplying cells for wound healing. Partaking in this complex system are the sebaceous, oil-secreting glands which are found in all types of skin and all over the body, but which are usually associated with a follicle. The sebaceous glands that resemble tree branches, are made up of a tube and one or two small sacs that are groups of smaller pockets called alveoli. They exist as tiny appendages to the hair follicles. When cells in the alveoli die and break apart excrete oil is produced which lubricates the hair and facilitate sweating in the follicle.

An important function of the present invention is to penetrate the surface of the skin down to the bottom of the follicle and to act as a revitalizing agent for the follicle as well as for the nerves, muscles alveoli and other parts associated with the production of hair and regeneration of cells.

While it is often considered to be a psychological or cosmetic problem, problems with excessive body hair or lack of body hair are likely as old as mankind. There are eastern religions that promote that all power of a human being is located in the hair of the scalp and that it renders a person powerless if the hair is cut or missing. The current invention does not relate to the removal of unwanted hair. It addresses the distinct areas of stimulation and restoration of hair and the area of skin regeneration for the purpose of wound healing.

Many more or less useless or even destructive methods have been brought forward with the purpose of restoring hair. The present invention presents a non-destructive method and device which in a natural way restores the ability of the follicles to function and properly perform their tasks without the use of force or abrasive agents.

It is previously know to utilize laser sources to expose the scalp area to electromagnetic radiation in order to prevent loss of hair, see for example in EP-0130950 and SE-510410. The first of these documents describes an arrangement containing one or two laser sources radiate a number of spots of the scalp area, through optical fibres. In accordance with the main embodiment, a large part of the scalp is thereby constantly under radiation without any intermissions for the purpose of recovery. According to another embodiment a laser source is caused to move across the scalp according to a predetermined trail. Such a treatment is time consuming and presents large difficulties in obtaining an even and uniform radiation over the entire scalp area.

SE-510410 on the other hand utilizes a number of laser sources line wise arranged in a helmet which can be rotated. The radiation is thereby in directed towards the scalp area alongside relatively narrow lines which pass over the area intended to be treated.

The method and device of the current invention was developed based on experience and observations relating to the behavior of the follicle area with respect to external stimulation. Certain substances such as hormones and vitamins exist in or are produced in the skin. The existence or production of substances necessary for the normal life cycle of skin and skin cells is also dependant upon light. Vitamin D for instance is produced by the skin while exposed to the rays of the sun. Although we usually cover our skin with clothes to protect it from the surrounding climate it is recognized that exposure to light and the sun can have a therapeutic effect on skin and skin tone. Pigmentation of the skin, eyes, and hair as an example is determined by the presence of melanin in cells of the epidermis which are called melanocytes. In addition to coloring melanin actually protects from excessive harmful UV rays by absorbing high-energy light more than it does other light in the spectrum.

SUMMARY OF THE INVENTION

Major factors relating to diminished or absent hair growth on the scalp are; i) insufficient circulation of blood in the scalp area; ii) dietary or nourishment related problems; iii) physical damage to the follicles or skin including clogging due to excessive oil secretion from the sebaceous glands or excessive production of waste products such as dandruff; iv) hormonal imbalances. This is a very simplified view and there can be a great number of reasons for problems in the area of loss or diminished growth of hair. Hair follicles are not continuously active and can enter different stages of rest and activity for reasons which are not completely known and which may occur several months after the events that triggered them.

The present invention addresses these and other problem areas in greater and lesser degree and proposes a method and laser operated device for therapeutic stimulation of skin which can be used for faster skin regeneration and revitalization of hair follicles for the purpose of rejuvenating skin, improving skin tone, assisting recoupment of irritated or damaged skin and enhancement of hair growth or regrowth. While optimizing the invention it has for instance been noticed that hair growth in a subject is intensified in direct relation to the actual path of a moving laser light source and that the desired effect of the invention is improved when a band of intermittent light obtained by the use of several laser diodes mounted in groups or in parallel expose the follicle area.

Stimulation in this context refers to a cajoling and balancing of the bodies own natural resources to heal rather than utilizing force of any kind. Just as there can be stimulation, there can be over stimulation with negative effects and too intense exposure to laser and similar light sources can have inflammatory effects while intermittent light as prescribed by the invention helps the skin control sebum production and other ailments thus acting as a natural anti-inflammatory agent. Observation shows further that the inflammatory phase of a wound or damaged tissue is accelerated rather than suppressed thus initiating a faster healing process. The effects of the invention in this respect can be explained to be direct, affecting the area being radiated, as well as indirect through initiation and acceleration of the bodies own healing process by drawing attention to the radiated area.

While earlier attempts have been made to utilize laser beams in the area of the stated purpose for this invention, this invention is directed to a new method of applying radiation from a light source, such as a laser, in order for such treatment to have a desired and reasonably predictable effect. The invention prescribes the use of a wave like, pulsating exposure as opposite to constant exposure to the light source in order to improve results and prevent unwanted effects.

Furthermore the present invention is directed at a device for the practical application and exposure of the skin according to the method of the invention. The device of the invention exposes the skin to intermittent light from an array of low power lasers which are rotated following a unique pattern in order to achieve a treatment surface which would otherwise require a much larger number of light emitting devices. In certain cases where a device is needed to be constructed at lower cost, light emitting diodes may be used instead and will give similar results provided that the time of exposure or the distance between the light source and the skin is adjusted accordingly.

In particular the present invention demonstrates the construction and use of such a device for the purpose of treating the scalp area of a person. The invention includes the use of a carefully designed helmet equipped with low power laser or light emitting diode devices which are mounted singularly or in groups and move according to a predetermined pattern as directed by the invention in order to reactivate and improve hair production from the hair follicles of the treated person. Similar devices, not intended for the scalp area and constructed according to the principle of the invention may be used to treat follicles in and in the vicinity of wounded skin in order to accomplish faster healing of wounds and to assist healing of wounds that have a tendency to heal slowly or not at all.

One embodiment of a device of the present invention utilized for the treatment of the follicles of the scalp area comprises an outer helmet and an inner helmet where the inner helmet is equipped with a number of low power laser modules. The inner helmet is mounted on a rail in such a way that it can move back and forth in one direction or the other. The rail as described may be fixed, alternatively, it is in itself movable in order to accomplish a non-linear path of light for the lasers exposing the scalp area of a head positioned in the helmet. Electric motors and electronic control circuits govern the movement of the inner helmet in such a way that the scalp area being under exposure receives an evenly distributed amount of laser or light emitting diode light. It is essential to the invention that it presents a way of using direct laser light exposure rather than light which has been diverted through an array of optical fibers. Furthermore the invention gives a guarantee that no single area is more exposed to laser light than any other. While the rotation of the inner helmet ensures that the complete scalp area is exposed to the laser or light emitting diode light, the system also causes the scalp area to be exposed in waves of light rather than constant exposure which increases the stimulatory effect at the same time as it decreases the risk for pain or discomfort to the person under treatment. It is believed that the pulsation in itself triggers the brain to give results.

The main purpose of the above embodiment of the invention is to provide a helmet equipped with light sources such as laser modules or light emitting diodes which can be used to expose the scalp area of a person to such light in order to stimulate and reactivate production of hair from the hair follicles of the scalp. This treatment in itself is designed to increase the circulation of blood in the follicle area and to cause nerve, muscle and other stimulation in order to enhance and speed up the normal life and production cycle of the follicles so exposed. The treatment is also aimed at assisting the accomplishment of a natural hormonal balance and normal secretion of the sebaceous glands.

The main purpose of a second embodiment of the invention is to provide a way of treating the follicles of any skin area with the same method. The device according to this embodiment therefore consists of an array of low power lasers or light emitting diodes which are turned of and on in such a way as to produce the effect of a wave like exposure.

Other embodiments of the invention have the same purpose but are constructed somewhat differently in that they emit light constantly but that the wave like exposure is achieved by a mechanical movement against and from the skin. This type of device is specifically useful in the case where light emitting diodes are used which gives less penetration than laser. By putting the light source very close to or in contact with the skin there is an increase in the effect and it also allows for less powerful light emitting devices. By massaging the skin blood is forced away from the area of contact allowing for deeper penetration by the light source which in some case is a wanted effect.

The invention also allows for a combination of therapies such as the use of specific oils or ointments together with the treatment prescribed by the invention as a manner of further increasing the effect of therapy. In this context treatment with minoxidil, finasterid and various forms of dehydrotestosteron blockers deserve specific mention as being auxiliary systems while in use together with the invention.

According to the invention the proper wave length of the laser light to accomplish the most beneficial results should be within the ranges of 400 nanometers to 1300 nanometers. The preferred wave length however is 670 nanometers. The power density distributed over the treated area may be as low as 0.9 J/cm2 and range up to 16 J/cm2 where 7–8 J/cm 2 can be a suitable value. It should be noted however that the effectiveness of the power density and wave lengths in use is a function between several influencing factors such as intensity, time of exposure, pulsation frequency etc. The preferred values mentioned above however are considered to be a "window" where the desired effects are most easily obtained.

The invention will be described in detail below with reference to the enclosed drawings giving examples of embodiments of the invention.

SHORT DESCRIPTION OF THE DRAWINGS

Figure 4:
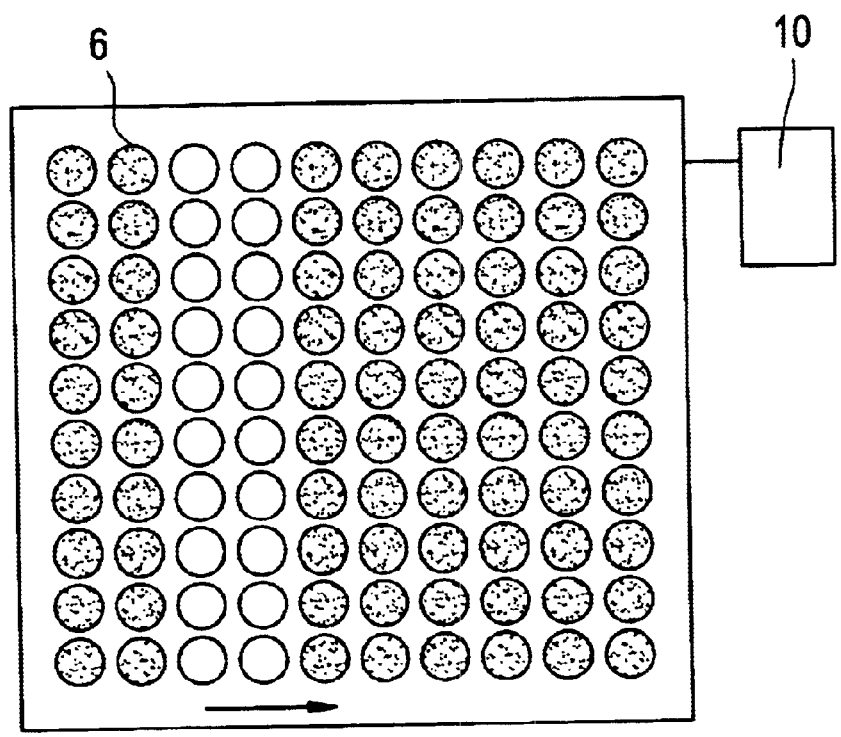

FIG. 4 schematically illustrates the principle of a fourth embodiment according to the invention.

Figure 5:
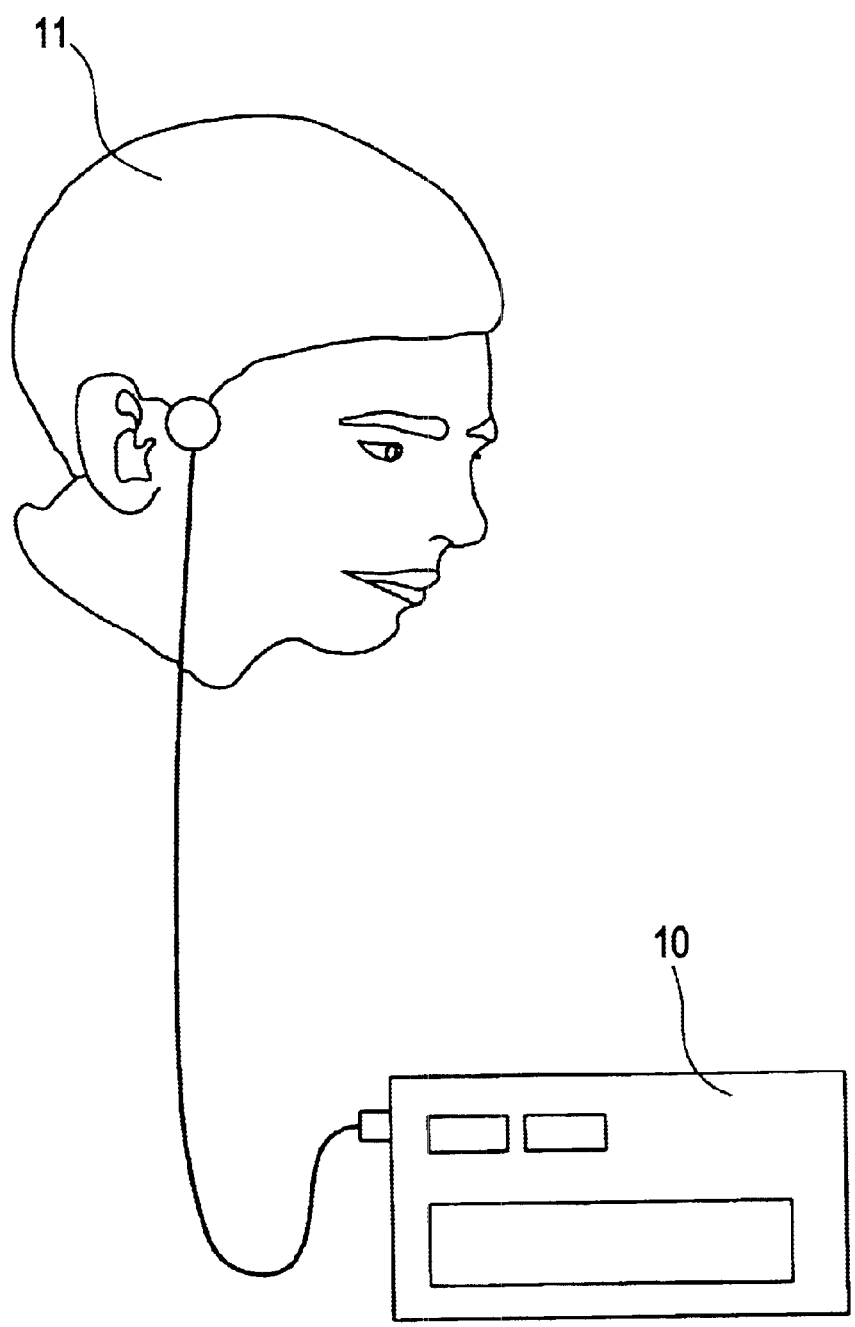
Figure 6:
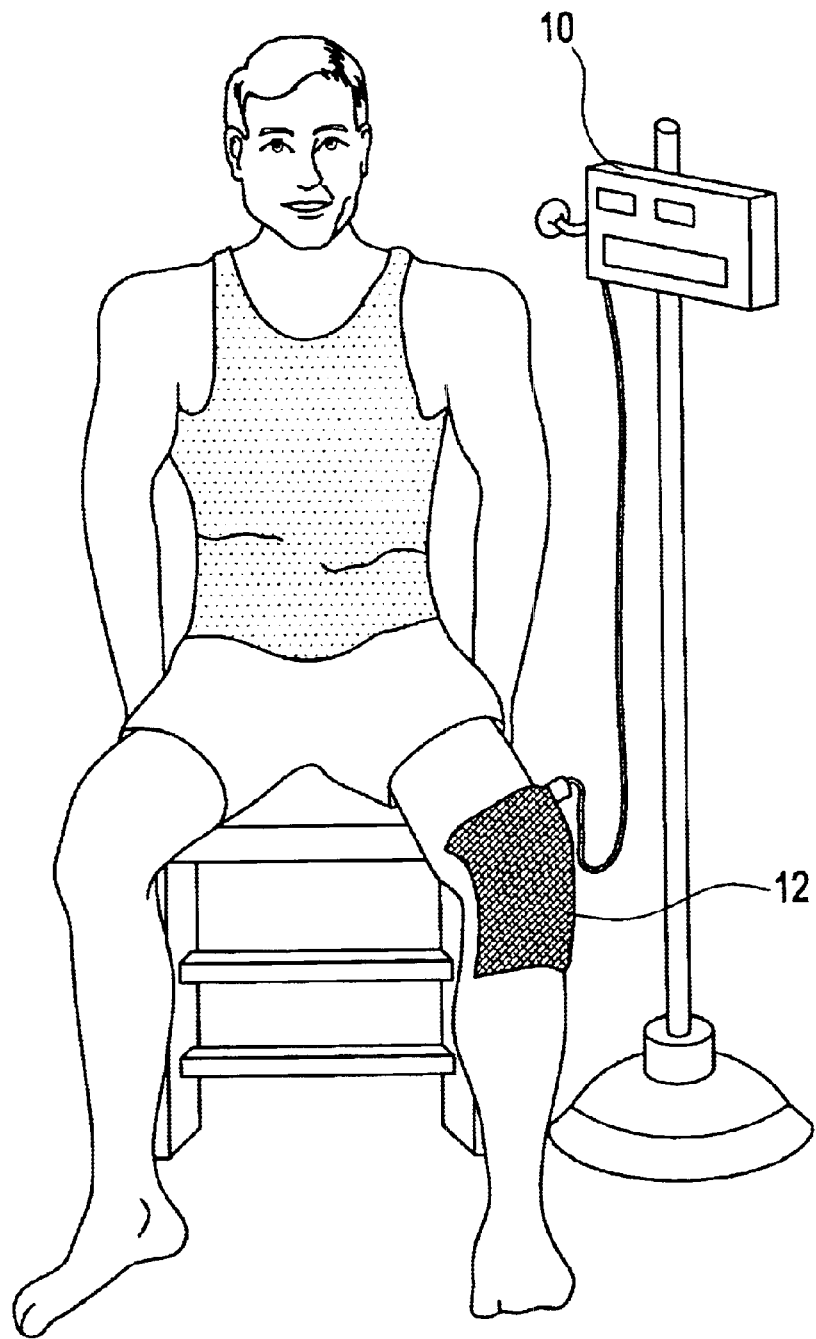

FIGS. 5 and 6 illustrate two alternative embodiments of a device according to FIG. 4.

FIGS. 7–10 illustrate two additional embodiments of devices according to the invention.

Figure 11:
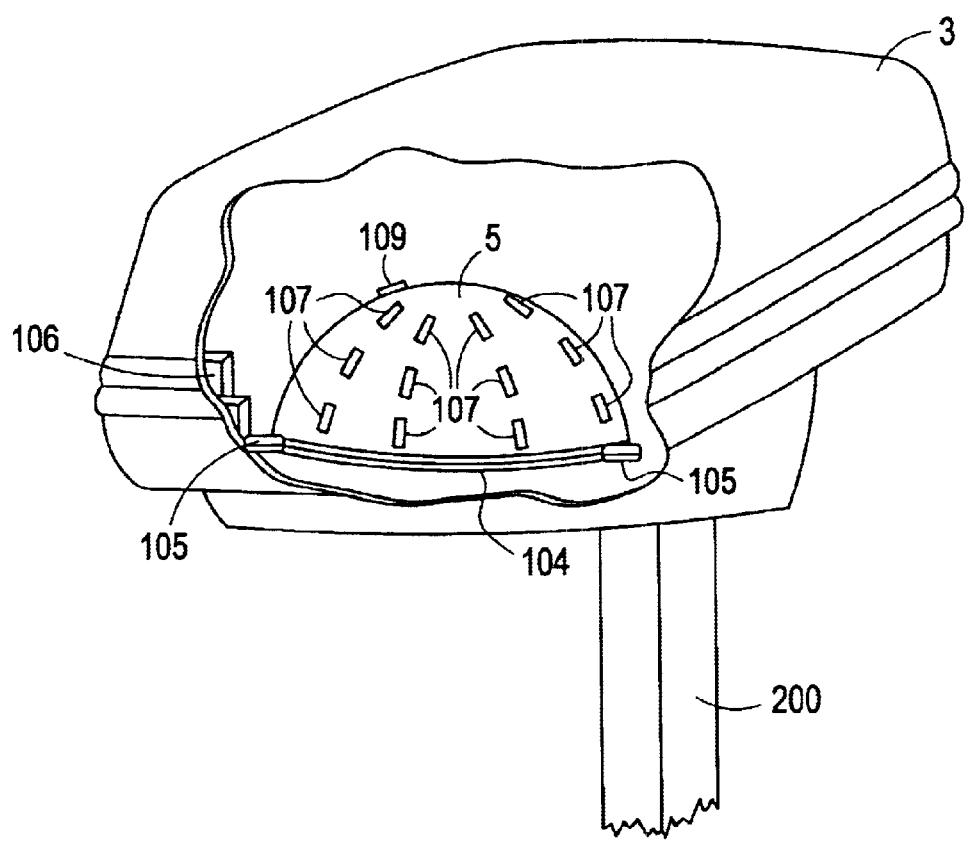

FIG. 11 illustrates a section through helmet showing the inner helmet placed in the outer canopy.

Figure 12:
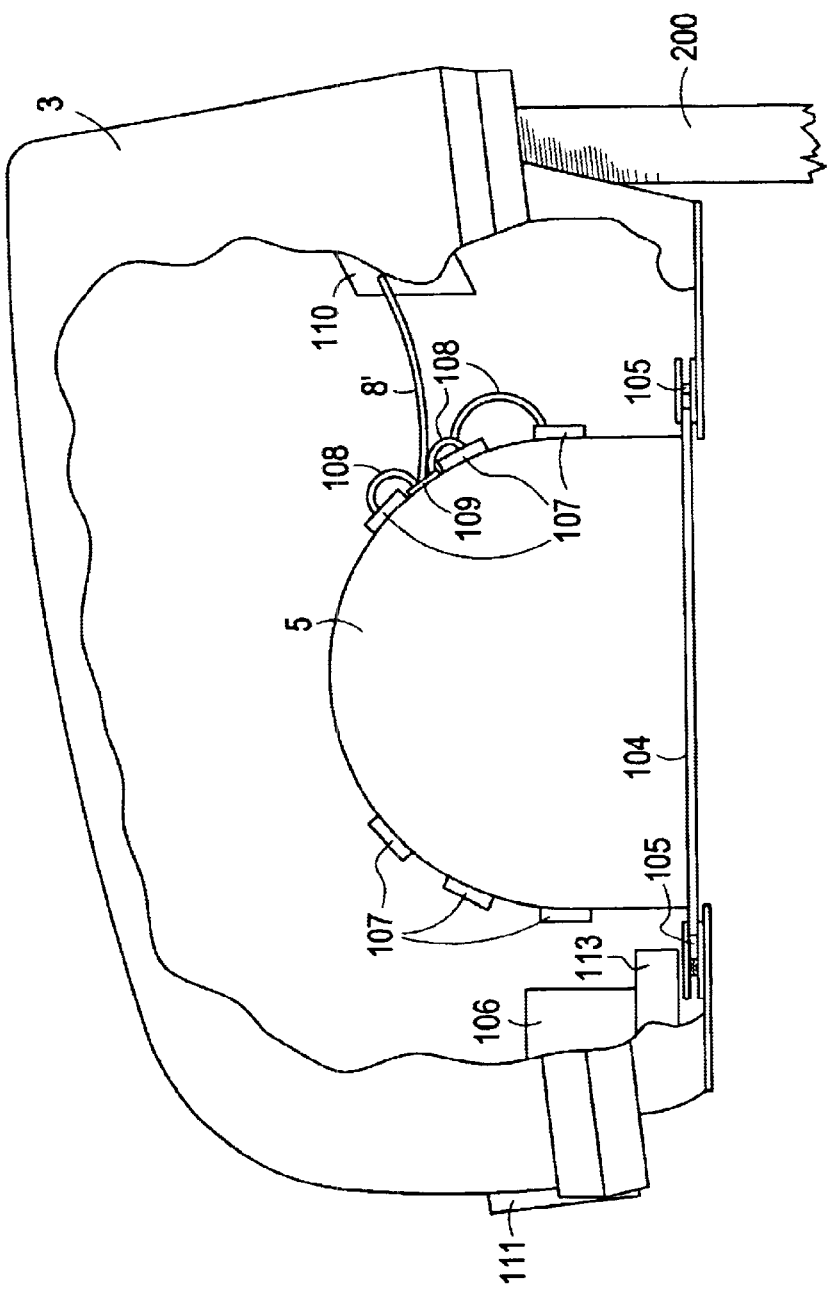

FIG. 12 illustrates a section from the side showing how the coupling is mounted to the inner helmet.

Figure 13A:
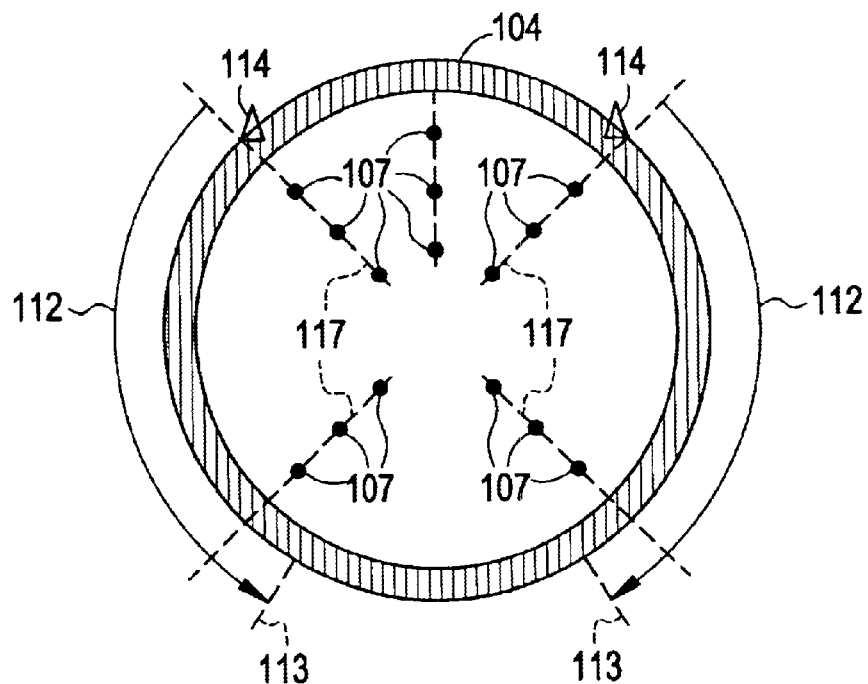

FIG. 13A illustrates a schematic view from above over the invention showing the turning movement of the inner helmet in relation to the positions of the laser diodes and how the laser diodes are placed in lines.

Figure 13B:
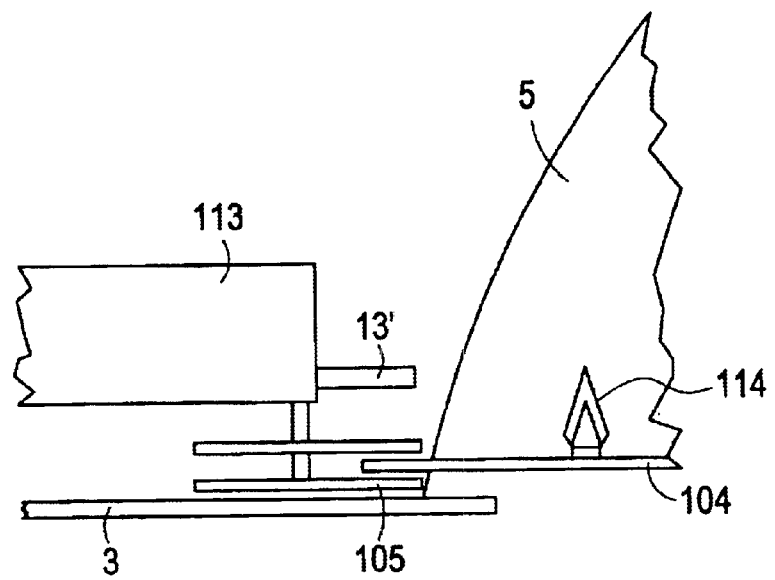

FIG. 13B illustrates how the inner helmet is suspended.

Figure 14:
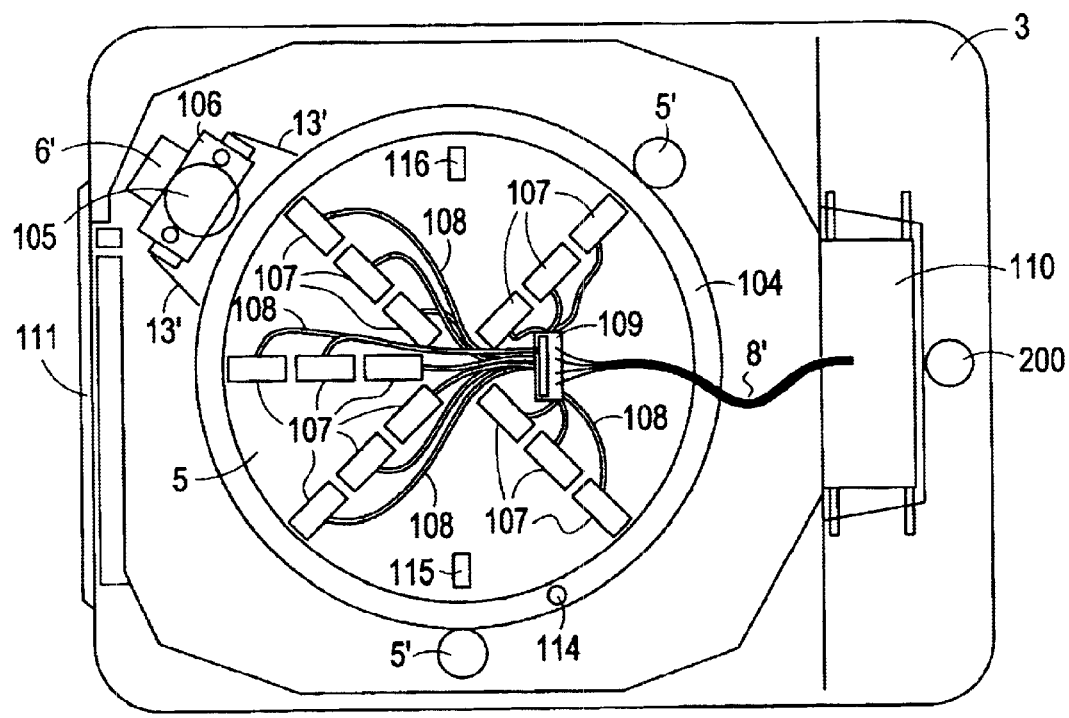

FIG. 14 illustrates in more detail how the inner helmet is coupled in relation to the drive motor and a circuit board.

DETAILED DESCRIPTION OF THE PREFERRED EMBODIMENTS

Figure 1:
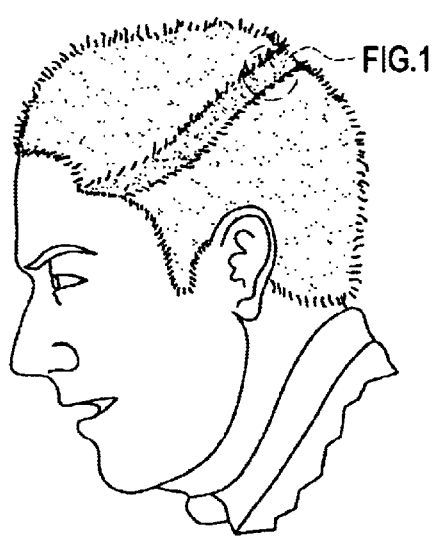
FIG. 1 illustrates a non-wanted effect of laser radiation which may result from the use of previously known devices.
Figure 1A:
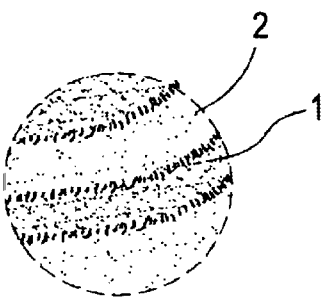

FIG. 1 shows a person who has been treated with radiation from laser diodes in order to stimulate hair growth. It is noted that the stimulation has varied in such a way that stronger hair growth has resulted in band like stripes 1 of the scalp area compared to areas 2 of less stimulation. This is a likely result when stimulation is made from laser diodes which move relative to the scalp area but where the emitted light fields do not sufficiently overlap each other. As an example, a risk for this would occur if the laser diodes are arranged adjacent to each other in a single row.

The invention is also based on the realization that stimulation preferably should be intermittent, that is to say, that the hair follicles in a certain area are stimulated for a period of time followed by a resting period followed by a renewed stimulation etc. While using single rows of e.g. laser diodes, it is likely difficult to achieve an optimum stimulatory period in relation to the intermediate resting periods.

This problem is resolved in the present invention by bringing about a band of light of a desired width. This band of light may be attained with the aid of light sources arranged along several mutually parallel lines, whereby the enlighted fields resulting from each individual light source overlap each other in order to create a band of light with a virtually homogenous intensity of radiation. The light sources placed along any such line are therefore preferably displaced relative to the light sources of adjacent lines.

Figure 2:
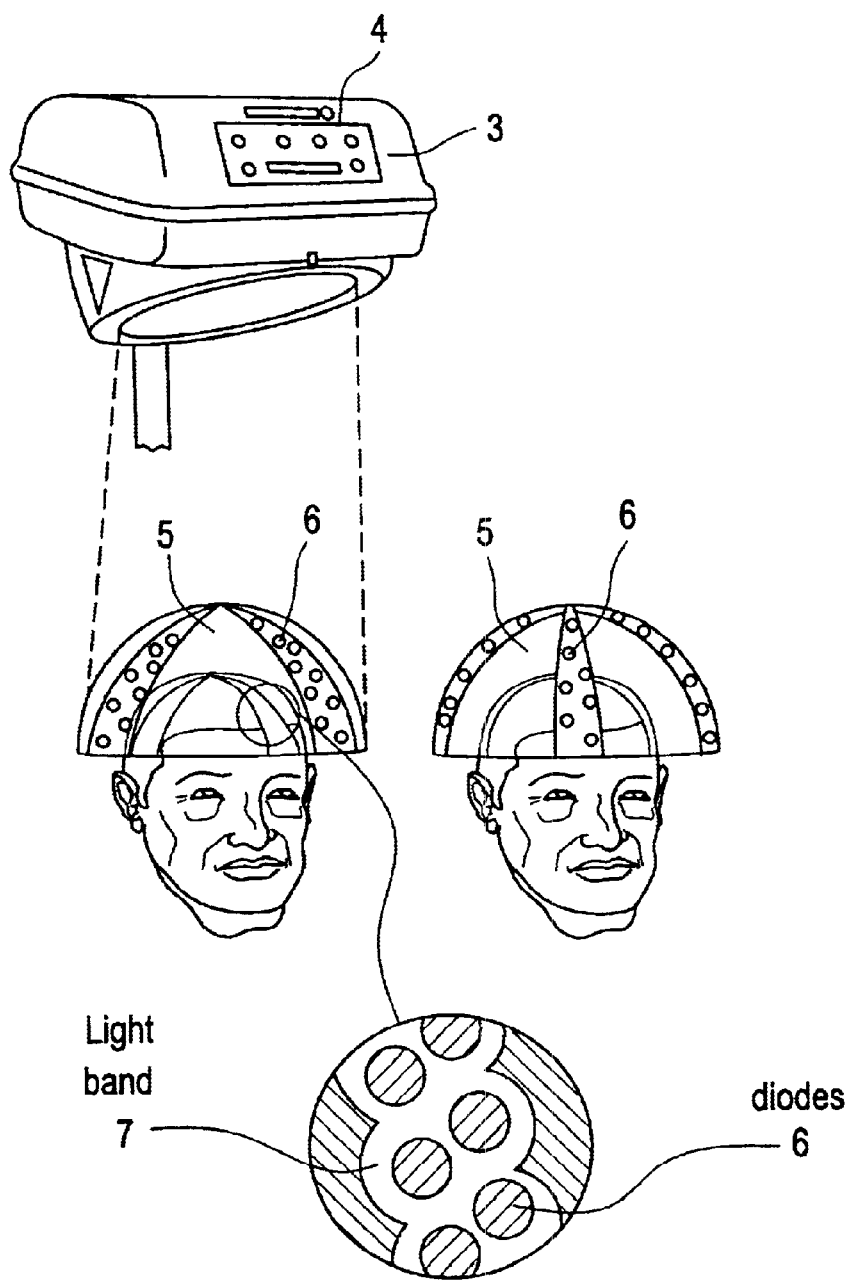
FIG. 2 illustrates a first embodiment of a device in accordance with the present invention.

FIG. 2 outlines a first embodiment of a device according to the invention. The embodiment comprises an outer canopy 3, with a panel 4 containing necessary control lights, controls etc. A helmet like arrangement is placed inside the canopy in such a way that it can be rotated back and forth a quarter of a circle above the head of the person being treated. For reasons of illustration, the helmet 5 is shown outside of the canopy 3. The bearing and rotation of the device may be accomplished in a manner which per se is previously know and which has been described in the patent SE-510 410 mentioned in the introduction of this application, and which is described below with reference to FIGS. 11–14.

FIG. 11 illustrates an electromagnetic radiation helmet comprising an outer canopy 1 mounted to a post 2 and an inner helmet 8 intended to be placed over the head in order to radiate. The outer canopy 1 acts as a protection for cables, drive motor, circuit board and drive wheels, see FIG. 12.

The laser diodes 1 on the helmet 3 are placed in vertical lines 17 which results in radiation along continuous vertical lines on the top of the head and the scalp. By means of the drive motor 6 the Inner helmet is turned alternately ¼ revolution. A relay 13 acts to have the motor to change direction by means of a stop member 14 at the rim 4 which hits a switch arm 13' which causes the relay to be opened alternately.

As the motor 6 which is mounted in the canopy 1 drives a drive wheel 5, the rim 4 on the inner helmet 3, supported by least two additional drive wheels 5', turns the inner helmet 3 alternately in both directions so that the laser diode modules 7 which are attached to the inner helmet 3 will lighten all the head placed in the helmet 3. FIG. 13B shows how the rim 4 runs against the drive wheel 5 which is driven by the motor via the shaft 6'.

The mounted laser diodes 7 are, via their cables 8, connected to a circuit board 9 which is connected to a main circuit board 10 via a cable 8', which main circuit board comprises a regulator for the control of the laser diodes 7, the front board 11, and the motor 6, of the inner helmet 3, see FIGS. 11–14.

In the helmet 3 there is a transmitter in the shape of a light diode 15 and a receiver in the shape of a phototransistor 16 which activates the laser diodes 7 when the canopy 3 is over a head. On the front board 11 there is a clock for setting the time of treatment.

On the inside of the helmet 5 there are several band shaped formations of laser diodes 6. The shown embodiment comprises four band shaped formations, each with the laser diodes 6 arranged in two lines. The laser diodes of each line are displaced relative to the diodes in an adjacent line a distance more or less corresponding to half the distance between two diodes in a line. This causes the areas being radiated to overlap in order to create a band shaped radiation area 7, which is moved back and forth across the scalp, in the example given corresponding to a twisting angle of a least 90 degrees. The twisting angle is determined by the number of band shaped arrangements of diodes 6. In FIG. 2, to the right, the helmet 5 is shown in a different phase of the rotation compared to what is shown to the left.

Instead of a back and forth rotating movement, the helmet 5 may of course be rotated continuously or intermittently in one direction or the other. In any of these manners of rotation it is accomplished that the hair follicles are stimulated during a certain period, followed by a resting period before a new period of stimulation. It is this alternation between periods of stimulation and rest which is sought after in the present invention.

FIG. 2 shows how stimulation is accomplished with radially extended bands of light 7. As an alternative the diodes 6 can be mounted in smaller groups, which are displaced from each other in the direction of the rotation in such a way that each group, during its rotation, creates alternating stimulatory periods and resting periods across a band 9 which extends in the direction of the rotation, see FIG. 3A.

The diodes 6 in each group are preferably arranged in at least two parallel rows each displaced relative to the other in order to accomplish the overlapping radiation areas.

Figure 3:
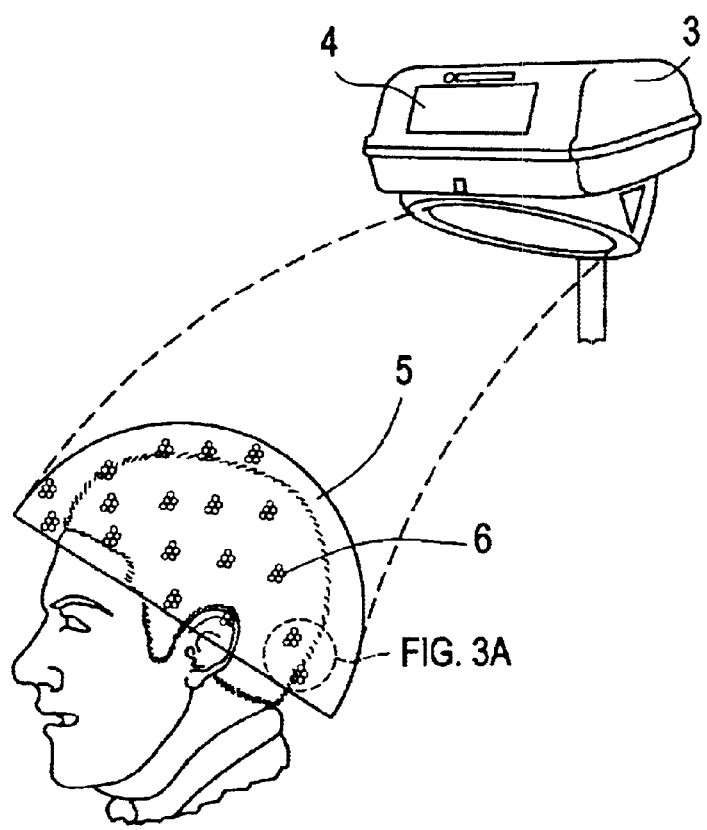
FIG. 3 illustrates a second embodiment of a device according to the invention.
Figure 3A:
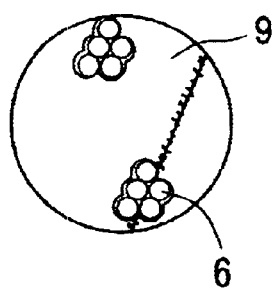
Figure 3B:
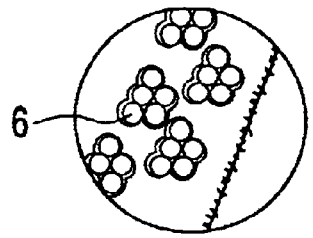

In order to make sure that there is no space between the bands 9 of radiation which is exposed with less intensity of stimulation than in the actual bands, the laser diodes 6 are preferably arranged in accordance with what is illustrated in FIG. 3B. In this arrangement the upper and lower diodes respectively overlap the corresponding diodes in the immediately trailing group. This way it is guaranteed that a uniform stimulation is achieved across the entire scalp area.

Although FIG. 2 as well as FIG. 3 has shown the utilization of two parallel rows of laser diodes 6 it is evident that a desired number of rows may be utilized.

As an alternative of having laser diodes move over the skin area intended to be treated, it is possible to utilize a large number of fixed laser diodes or light emitting diodes, which cover a desired area and which are selectively activated in order to create a band of radiation which travels across the skin surface. This is illustrated in FIG. 4, an embodiment which comprises a large number of light emitting diodes 6 which are switched on and off as governed by a control unit 10. The illustration of the embodiment shows two rows of light emitting diodes 6, in this instance row number three and four from the left, as unfilled circles to indicate that they are activated and which create a uniform band of light radiation upon the underlying skin surface. As governed by the control unit 10 the diodes of row three may be deactivated after a certain time period and the diodes of row 5 be activated whereby the band of radiation is caused to move across the skin area without the need for the arrangement of diodes to be moved. It is also possible to accomplish that several bands of radiation are moved concurrently in the same or different directions across the skin area.

An embodiment of this technique is illustrated in FIG. 5, where the scalp area of the person intended to be treated is covered with a flexible carrier 11, in the illustrated example in the form of a cap, for a large number of light emitting diodes (not shown), The light emitting diodes are arranged on the inside of the carrier 11 and are sequentially activated with the aid of the control unit 10 in order to accomplish that one or more bands of radiation are moved in a desired direction and speed across the scalp in order to achieve the alternating stimulation and resting periods as desired.

Examples have been given above of how the invention is utilized for the purpose of stimulating growth of hair of the scalp area. As mentioned in the introduction, a stimulation of the hair follicles of other places of the body may have a positive influence for example on certain healing processes. FIG. 6 is a schematic illustration of an embodiment according to FIG. 4 in which a flexible carrier 12 is placed over the knee area of a person. The inner surface of the carrier 12 comprises laser diodes or light emitting diodes which are activated sequentially in the same way as described in connection with FIG. 5 in order to accomplish that one or more bands of radiation are moved over the skin and result in a healing stimulatory effect of the hair follicles of the treated area. As described previously the activation of the diodes is done from a control unit 10.

In the utilization of light emitting diodes in stead of laser diodes it is commonly the case, due to the lower effect of the light emitting diodes, that these in principle are placed in contact with the skin area where the hair follicles are going to be stimulated. This can be achieved with the aid of, as is very schematically shown in FIG. 7, a curved device which comprises a large number of light emitting diodes 13 arranged in rows. This is also shown in FIG. 8 which gives an end view of the embodiment according to FIG. 7. In this embodiment, the diodes are arranged in such a way that only the diodes 13 of three rows are in contact with the skin 14 at the same time. Even if all diodes would be activated it is therefore only the diodes of these rows that may accomplish a stimulating effect worth mentioning. Thus, by rolling the device 15 back and forth, the diodes 13 of different rows, are brought in contact with the skin 14 to accomplish a stimulating effect of its hair follicles. This embodiment as well will thus, through such a rolling motion, accomplish the activation of a band of radiation which is moved across the skin in pace with the rolling motion.

Figure 7:
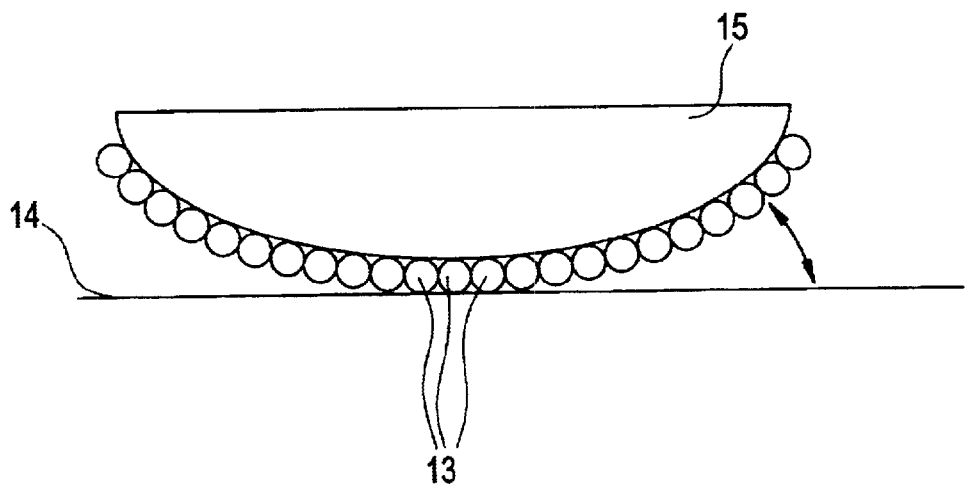
Figure 8:
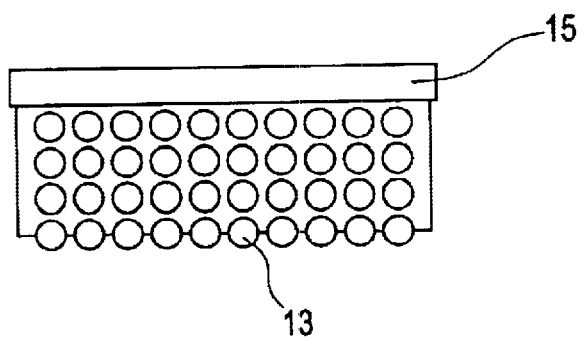

A further advantage with the embodiment as shown in FIGS. 7 and 8 is that the diodes 13, which in a given moment of time are creating a stimulating effect of the hair follicles of the skin 14, also are giving the skin a certain element of massage which has been found to increase stimulation thereby improving the usefulness of the radiation.

Figure 9:
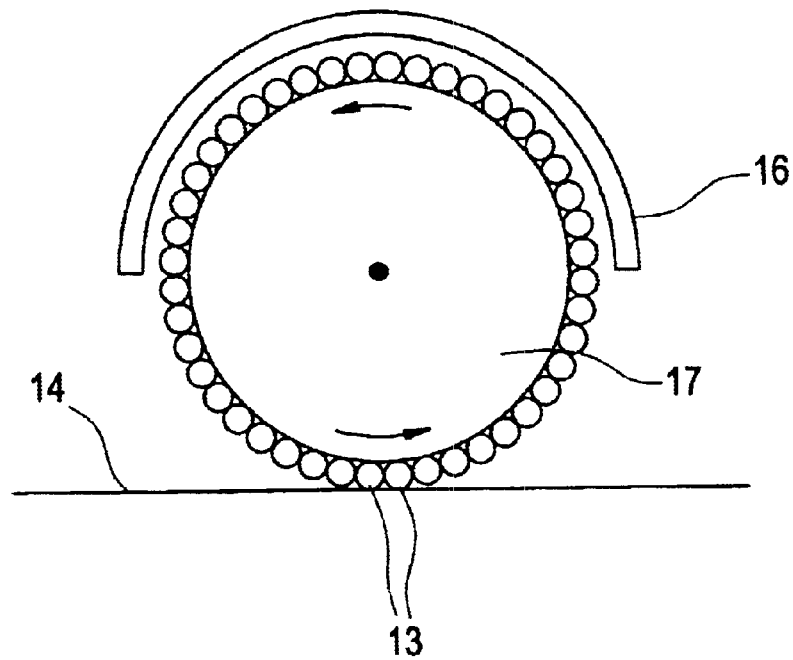
Figure 10:
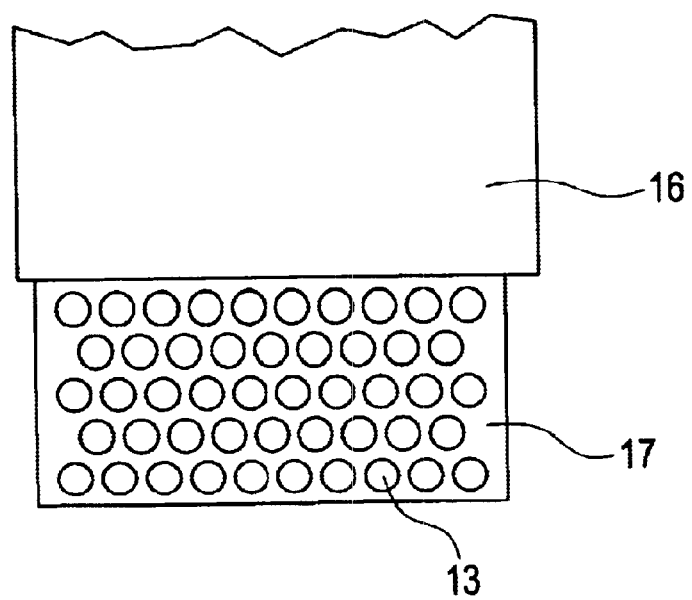

FIGS. 9 and 10 show an embodiment with a corresponding effect as described in connection with FIGS. 7 and 8. In FIGS. 9 and 10, the diodes 13 are arranged along parallel lines on a rotating cylinder 17 with a part 16 which acts as a light blocking screen.

As is shown in FIG. 9, only the diodes of two adjacent rows are in contact with the skin 14 at the same time. These two rows of diodes are thus creating a stimulating band of radiation which is moved across the skin in pace with the rotation of the cylinder 17 which causes successive rows of diodes to be in contact with the skin. Also in this case there is a concurrent massaging effect on the skin. Preferably the diodes of adjacent rows are displaced in relation to each other in order for their respective radiation areas to overlap in order to create a uniform stimulation of the hair follicles. The same goes for the embodiment according to FIGS. 7 and 8.

As stated above one normally aims at a uniform radiation of the skin area in question. In certain cases it may however be desirable to accomplish a varying stimulation, for example in the case of hair loss to increase stimulation on areas which are more deficient of hair than others. This can easily be accomplished through the utilization of diodes of varying effects on some areas or by varying the number of rows of activated diodes or the density of the placement of diodes. Where there is an electronically controlled diode matrix the control program can simply be changed in order to accomplish the desired variations in radiation intensity.

As an alternative to the arrangement of laser diodes or other light emitting diodes in close connection to or in contact with the skin, these can be placed at a distance from the skin and the light be conducted to the skin through optical fibres.

A number of embodiments of the invention have been described above. These embodiments can be varied from several aspects within the framework of the given claims as is easily recognizable by an expert in the area.

What is claimed is:

1. A method of stimulating the hair follicles of a skin area by radiation of light, comprising the following steps:
    a. arranging a number of sources of light in at least two more or less parallel rows of light sources wherein the light sources of one row are offset in relation to the light sources of another row by approximately half of the distance between the light sources in the one row so as to expose a portion of the area of skin to a field of light in the shape of a band, and
    b. moving of the band shaped field of light repeatedly over the area of skin to be treated in order to create a pulsating stimulation of the hair follicles of the skin area.

2. A method according to claim 1 in which a band of light is moved by moving light sources arranged in a way so as to create the band of light.

3. A method according to claim 1 in which a band of light is transferred through sequential on and off switching of light sources, in an arrangement of light sources covering the area of skin to be treated, in such a way that activated light sources cause a band of light to sweep through the arrangement.

4. A method according to claim 1 in which a band of light is moved by successively repositioning light emitting diodes of an arrangement of light emitting diodes which are successively repositioned from a passive to an active exposure status by moving the diodes closer to and further away from the skin area in a way so as to continuously cause a band of light emitting diodes to come into the active exposure status.

5. A method according to claim 1 in which the exposing of a portion of the area of skin to a field of light is combined with a consecutive massaging of the skin area being exposed.

6. A device for the purpose of stimulating hair follicles of a skin area through exposure of light, comprising:
    a number of light sources positioned in at least two more or less parallel rows of light sources wherein the light sources of one row are offset in relation to the light sources of another row by approximately half of the distance between the light sources in the one row in order to radiate in a band like portion of the area of the skin; and
    means for moving the band of radiation repeatedly across the area of skin being treated in order to create a pulsating stimulation of the hair follicles of the skin area,
    wherein the light sources are positioned in an arrangement which covers the entire area of skin intended to be treated, and where the device comprises switching elements designed to successively switch on and off light sources within the arrangement to accomplish that a band of radiation from activated light sources repeatedly moves across the skin area.

7. A device according to claim 6 in which the light sources comprise laser diodes which are positioned in a band like formation and which device comprises means for moving the aforementioned band like formation of laser diodes across the area of skin which is intended to be treated.

8. A device for the purpose of stimulating hair follicles of a skin area through exposure of light, comprising:
    a number of light sources positioned in order to radiate in a band like portion of the area of the skin; and
    means for moving the band of radiation repeatedly across the area of skin being treated in order to create a pulsating stimulation of the hair follicles of the skin area,
    wherein the light sources comprise light emitting diodes which are positioned in at least two more or less parallel rows of light emitting diodes wherein the light emitting diodes of one row are offset in relation to the light emitting diodes of another row by approximately half of the distance between the light emitting diodes in the one row and which arrangement is moveable relative to the skin area intended to be treated, and where the device comprises means for repositioning the arrangement to accomplish that the light emitting diodes are successively moved from a passive to an active state of exposure through being brought closer to or further from the skin area in a manner such that at each instant a band of light emitting diodes are in the aforementioned active state of exposure which move across the skin area.

9. A device according to claim 8 in which the at least two rows of light emitting diodes are positioned in a band like formation.

10. A device for the purpose of stimulating hair follicles of a skin area through exposure of light, comprising:

a number of light sources positioned in order to radiate in a band like portion of the area of the skin;

means for moving the band of radiation repeatedly across the area of skin being treated in order to create a pulsating stimulation of the hair follicles of the aforementioned skin area; and an exterior hood, a helmet shaped device inside the exterior hood which is mounted on ball bearings so that it can be rotated, and the number of light sources are positioned so as to form at least one band shaped formation mounted on the aforementioned helmet shaped device wherein each and every one of the band shaped formations of light sources comprise at least two more or less parallel rows of light sources wherein the light sources of one row are offset in relation to the light sources of another row by approximately half of the distance between the light sources in the row first mentioned.

11. A device according to claim 10 wherein said at least one band shaped formation of light emitting diodes comprises at least three separately mounted band shaped formations of light emitting diodes.

12. A device according to claim 10 in which the light emitting diodes closest to a center of rotation of the band shaped formation of light emitting diodes output lower light effect relative to the light emitting diodes furthest from the center of rotation.

* * * * *